United States Patent
Jacobs (10) Patent No.: US 9,519,754 B2
(45) Date of Patent: Dec. 13, 2016

(54) APPARATUSES AND METHODS FOR PARALLEL ANALYTICS

(75) Inventor: Michael N. Jacobs, Jordan, MN (US)

(73) Assignee: OPTUMINSIGHT, INC., Eden Prairie, MN (US)

( * ) Notice: Subject to any disclaimer, the term of this patent is extended or adjusted under 35 U.S.C. 154(b) by 547 days.

(21) Appl. No.: 13/157,622

(22) Filed: Jun. 10, 2011

(65) Prior Publication Data

US 2011/0307528 A1 Dec. 15, 2011

Related U.S. Application Data

(60) Provisional application No. 61/353,907, filed on Jun. 11, 2010.

(51) Int. Cl.
*G06F 17/30* (2006.01)
*G06F 19/00* (2011.01)

(52) U.S. Cl.
CPC ....... *G06F 19/328* (2013.01); *G06F 17/30289* (2013.01)

(58) Field of Classification Search
CPC ................................. G06F 17/30289
USPC ............................. 707/791, 802, 803, 809, 812,707/999.101–107; 718/105; 712/226
See application file for complete search history.

(56) References Cited

U.S. PATENT DOCUMENTS

| | | | |
|---|---|---|---|
| 4,394,137 A | 7/1983 | Marion et al. | |
| 7,650,331 B1 | 1/2010 | Dean et al. | |
| 2005/0281736 A1 | 12/2005 | Bedetti | |
| 2006/0294038 A1* | 12/2006 | Grossfeld et al. | 707/1 |
| 2007/0179927 A1* | 8/2007 | Vaidyanathan et al. | 707/1 |
| 2007/0226342 A1 | 9/2007 | Apelbaum | |
| 2008/0021987 A1 | 1/2008 | Bates et al. | |
| 2009/0089560 A1* | 4/2009 | Liu et al. | 712/226 |
| 2009/0089658 A1* | 4/2009 | Chiu et al. | 715/234 |
| 2010/0095303 A1* | 4/2010 | Archer et al. | 718/105 |

OTHER PUBLICATIONS

"Apache Hadoop," Mar. 19, 2012, accessed from <http://hadoop.apache.org> on Jun. 26, 2012.

(Continued)

*Primary Examiner* — Syling Yen
(74) *Attorney, Agent, or Firm* — Seyfarth Shaw LLP; Brian Michaelis; Christopher Baxter (57) ABSTRACT

Methods, apparatus, and software packages for data processing are disclosed. In some embodiments, the method may include receiving a dataset. In some embodiments, the method may include determining a control number of a processing system. In some embodiments, the control number may include a number of evaluation units within the processing system. The method may include processing the dataset using a plurality of evaluation units. In some embodiments, processing the dataset may include allocating a free evaluation unit to form a busy evaluation unit. Processing the dataset may also include creating a data subdivision for the busy evaluation unit, the data subdivision including a part of the dataset. Processing the dataset may also include evaluating the data subdivision. Processing the dataset may also include releasing the busy evaluation unit. The allocating, creating, evaluating, and releasing may performed concurrently by the plurality of evaluation units.

33 Claims, 6 Drawing Sheets

(56) References Cited

OTHER PUBLICATIONS

"JPPF," 2001, accessed from <http://www.jppf.org> on Jun. 26, 2012.
"MapReduce," *Wikipedia, The Free Encyclopedia. Wikimedia Foundation, Inc.*, Jun. 21, 2012, accessed from <http://en.wikipedia.org/wiki/MapReduce> on Jun. 26, 2012.
"OS Workflow Overview," Opensymphony, Mar. 16, 2009, accessed from <http://web.archive.org/web/20090316065829/http://www.opensymphony.com/osworkflow/> on Jun. 26, 2012.
"Spring Batch Features and Roadmap," May 13, 2011, accessed from <http://static.springsource.org/spring-batch/features.html> on Jun. 26, 2012.
"Spring Batch," Nov. 21, 2011, accessed from <http://static.springsource.org/springbatch/index.html> on Jun. 26, 2012.
"Spring Framework," accessed from <http://static.springsource.org/spring-batch/reference/html/scalability.html> on Jun. 26, 2012.
"Welcome to Apache Pig!" Apr. 26, 2012, accessed from <http://pig.apache.org/> on Jun. 26, 2012.
Amalo, "PLINQ and Office Add-ins," Microsoft Corporation, 2010.
Dean and Ghemawat, "MapReduce: Simplified Data Processing on Large Clusters," *OSDI'04: Sixth Symposium on Operating System Design and Implementation, San Francisco, CA, Dec. 2004*.
George et al., "Optimizing Parallel Applications Using Concurrency Visualizer: A Case Study," Microsoft Corporation, 2010.
Hoag, "A tour of various TPL Options," Microsoft Corporation, 2009.
International Search Report and Written Opinion issued in PCT/US11/39952, dated Oct. 13, 2011.
Liddell, "Using Cancellation Support in .NET Framework 4," Microsoft Corporation, 2010.
Omara, "Performance Characteristics of New Synchronization Primitives in the .NET Framework 4," Microsoft Corporation, 2010.
Ostrovsky, "Parallel Programming in .NET 4: Coding Guidelines," Microsoft Corporation, 2010.
Song et al., "Thread-safe Collections in .NET Framework 4 and their performance characteristics," Microsoft Corporation, 2009.
Tan, "PLINQ's ordering model," Microsoft Corporation, 2010.
Vagata, "When Should I Use Parallel.ForEach? When Should I use PLINQ?" Microsoft Corporation, 2010.
Verenkar, "Using .NET4 Parallel Programming Model to Achieve Data Parallelism in Multi-tier Application," Microsoft Corporation, 2010.
Wo and Manu, "Parent-Child Task Relationships in the .NET Framework 4," Microsoft Corporation, 2009.
Wo and Manu, Workflow and ParallelExtensions in .NET Framework 4, Microsoft Corporation, 2009.
International Preliminary Report on Patentability of International Application PCT/US2011/039952, dated Dec. 27, 2012.
Yinfei, Pan, et al. A Static Load-Balancing Scheme for Parallel XML Parsing on Multicore CPUs. 7th IEEE International Symposium on Cluster Computing and the Grid. pp. 351-362. 2007.
EP Search Report for EP 11793229.3.

* cited by examiner

APPARATUSES AND METHODS FOR PARALLEL ANALYTICS

CROSS-REFERENCE TO RELATED APPLICATIONS

This application claims the benefit of U.S. Provisional Application No. 61/353,907 filed Jun. 11, 2010, the entire contents of which is specifically incorporated herein by reference without disclaimer.

BACKGROUND OF THE INVENTION

Field of the Invention

This invention relates to methods, systems, and apparatuses for data processing and management, and more particularly to a configurable framework for processing parallel analytics.

Summary of the Invention

The healthcare industry is under a high level of scrutiny to reduce overall costs and improve quality. Critical to these improvements is the automated evaluation of insurance coverage, conformity of the services compared to the best practices, opportunities for prevention, quality of care measurements and managed care interventions and detection of fraudulent or incorrect claims. Unfortunately, the healthcare industry is faced with missing or incorrect clinical or demographic information as well as an enormous volume of data for patients, dependents, and the claims for their care.

A large health plan with 34 million members can typically have over two billion claims over a three year period. Because of missing or incorrect information, this data must be reprocessed several times before it meets business requirements. Historical solutions have had difficulties completing several rounds of processing within a month. Reducing the processing times of this automation may (1) help reduce the accounts receivable backlogs of payers and providers, enabling them to be more financially secure, (2) more readily find incorrect or fraudulent claims in an environment of decreasing Medicare reimbursements, (3) enable earlier proactive managed care interventions to keep patients healthy, avoiding the much higher costs of an emergency room visit or costly complication later, (4) increasing other business process velocity by providing quality results more quickly, and more efficiently. Though the systems, methods, and apparatuses disclosed herein may be used to process healthcare claims and similar data, the disclosure is not so limited—any datasets, healthcare or otherwise, may be received and processed.

Prior art solutions have been developed to tackle this problem. For example, U.S. Pat. No. 7,650,331 describes a "System and Method for Efficient Large-Scale Data Processing" to Dean et al. The systems and methods described here are based on a "map/reduce" programming model and an associated implementation for processing and generating large datasets. The Dean disclosure describes completely subdividing input data into several map tasks and subsequently assigning those tasks to various processes. Such initial subdivision of all work tasks before assignment to various process can be both time consuming and resource intensive.

SUMMARY OF THE INVENTION

Systems, methods, and apparatuses for processing data processing are disclosed. The systems, methods, and apparatuses disclosed herein enable efficient work subdivision of received input datasets.

In some embodiments, the method may include receiving a dataset. In some embodiments, the method may further include determining a control number of a processing system. In some embodiments, the control number may include a number of evaluation units within the processing system. The method may further include processing the dataset using a plurality of evaluation units. In some embodiments, processing the dataset may include allocating a free evaluation unit to form a busy evaluation unit. In some embodiments, processing the dataset may also include creating a data subdivision for the busy evaluation unit, the data subdivision including a part of the dataset. In some embodiments, processing the dataset may also include evaluating the data subdivision. In some embodiments, processing the dataset may also include releasing the busy evaluation unit. In some embodiments, one or more of the allocating, creating, evaluating, and releasing steps may performed concurrently by the plurality of evaluation units.

In some embodiments, processing the dataset may be repeated by the plurality of evaluation units until completion.

In some embodiments, the evaluation unit may include one or more processing devices.

In some embodiments, the data subdivision may include one or more subtasks.

In some embodiments, evaluating the data subdivision may further include evaluating one or more subtasks.

In some embodiments, evaluating the data subdivision may further include describing the data subdivision with an XML framework.

In some embodiments, describing the dataset with an XML framework may further include ordering dependencies of the one or more subtasks to form one or more dependent subtasks.

In some embodiments, evaluating the data subdivision may further include producing intermediate results. In some embodiments, evaluating the data subdivision may further include sharing the intermediate results with the one or more dependent subtasks.

In some embodiments, creating the data subdivision may include recursively creating nested data subdivisions.

In some embodiments, creating the data subdivision may include using a one or more configurable subdivision strategies.

In some embodiments, determining the control number may include using configuration rules.

In some embodiments, determining the control number may further include determining available compute resources.

In some embodiments, determining the control number may also include determining available compute resources in response to the configuration rules.

In some embodiments, determining the control number may also include determining the control number in response to the memory size and the one or more processing devices.

In some embodiments, the method may further include using one or more configurable control number strategies.

In some embodiments, evaluating the data subdivision, may further include estimating the evaluation duration and measuring the evaluation duration. In some embodiments, the method further comprising sending status messages.

A apparatus for data processing is also disclosed. In some embodiments, the apparatus may include a receive module configured to receive a dataset. In some embodiments, the apparatus may include a control module configured to determine a control number of a processing system. In some embodiments, the control number may include a number of evaluation units within the processing system. In some embodiments, the apparatus may include a data system module configured to process the dataset using a plurality of evaluation units. In some embodiments, processing the dataset may include allocating a free evaluation unit to form a busy evaluation unit. In some embodiments, processing the dataset may include creating a data subdivision for the busy evaluation unit, the data subdivision comprising a part of the dataset. In some embodiments, processing the dataset may include evaluating the data subdivision. In some embodiments, processing the dataset may include releasing the busy evaluation unit. In some embodiments, one or more of the allocating, creating, evaluating, and releasing steps are performed concurrently by the plurality of evaluation units.

In some embodiments of the apparatus, processing the dataset may be repeated by the plurality of evaluation units until completion.

In some embodiments of the apparatus, the evaluation unit may include one or more processing devices.

In some embodiments of the apparatus, the data subdivision comprises one or more subtasks.

In some embodiments of the apparatus, evaluating the data subdivision may include evaluating one or more subtasks.

In some embodiments of the apparatus, evaluating the data subdivision further may include describing the data subdivision with an XML framework.

In some embodiments of the apparatus, describing the dataset with an XML framework further may include ordering dependencies of the one or more subtasks to form one or more dependent subtasks.

In some embodiments of the apparatus, evaluating the data subdivision may include producing intermediate results and sharing the intermediate results with the one or more dependent subtasks.

In some embodiments of the apparatus, creating the data subdivision may include recursively creating nested data subdivisions.

In some embodiments of the apparatus, creating the data subdivision may include using a one or more configurable subdivision strategies.

In some embodiments of the apparatus, determining the control number may include using configuration rules.

In some embodiments of the apparatus, determining the control number further may include determining available compute resources.

In some embodiments of the apparatus, determining the control number further may include determining available compute resources in response to the configuration rules.

In some embodiments of the apparatus, determining the control number further may include determining the control number in response to the memory size and the one or more processing devices.

In some embodiments of the apparatus, determining the control number further may include using one or more configurable control number strategies.

In some embodiments of the apparatus, evaluating the data subdivision further may include estimating the evaluation duration and measuring the evaluation duration.

Some embodiments of the apparatus may further include a module for sending status messages.

A computer program product is also disclosed. The computer program product may include a computer readable medium having computer usable program code executable to perform operations for processing data, the operations of the computer program product. Some embodiments of the computer program product may include receiving a dataset. Some embodiments of the computer program product may include determining a control number of a processing system, where the control number comprises a number of evaluation units within the processing system. Some embodiments of the computer program product may include processing the dataset using a plurality of evaluation units. In some embodiments of the computer program product, processing the dataset may include allocating a free evaluation unit to form a busy evaluation unit. In some embodiments of the computer program product, processing the dataset may include creating a data subdivision for the busy evaluation unit. In some embodiments of the computer program product, the data subdivision may be a part of the dataset. In some embodiments of the computer program product, processing the dataset may include evaluating the data subdivision. In some embodiments of the computer program product, processing the dataset releasing the busy evaluation unit. In some embodiments of the computer program product, one or more of the allocating, creating, evaluating, and releasing steps are performed concurrently by the plurality of evaluation units.

In some embodiments of the computer program product, processing the dataset may be repeated by the plurality of evaluation units until completion.

In some embodiments of the computer program product, an evaluation unit may include one or more processing devices.

In some embodiments of the computer program product, the data subdivision may include one or more subtasks.

In some embodiments of the computer program product, evaluating the data subdivision may include evaluating one or more subtasks.

In some embodiments of the computer program product, evaluating the data subdivision further may include describing the data subdivision with an XML framework.

In some embodiments of the computer program product, describing the dataset with an XML framework further may include ordering dependencies of the one or more subtasks to form one or more dependent subtasks.

In some embodiments of the computer program product, evaluating the data subdivision further may include producing intermediate results and sharing the intermediate results with the one or more dependent subtasks.

In some embodiments of the computer program product, creating the data subdivision may include recursively creating nested data subdivisions.

In some embodiments of the computer program product, creating the data subdivision may include using a one or more configurable subdivision strategies.

In some embodiments of the computer program product, determining the control number may include using configuration rules.

In some embodiments of the computer program product, determining the control number further may include determining available compute resources.

In some embodiments of the computer program product, determining the control number further may include determining available compute resources in response to the configuration rules.

In some embodiments of the computer program product, determining the control number further may include determining the control number in response to the memory size and the one or more processing devices.

In some embodiments, the computer program product may include using one or more configurable control number strategies.

In some embodiments of the computer program product, evaluating the data subdivision further may include: estimating the evaluation duration and measuring the evaluation duration.

In some embodiments of the computer program product, may send status messages.

The term "coupled" is defined as connected, although not necessarily directly, and not necessarily mechanically.

The terms "a" and "an" are defined as one or more unless this disclosure explicitly requires otherwise.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Certain units described in this specification have been labeled as modules, in order to more particularly emphasize their implementation independence. A module is "[a] self-contained hardware or software component that interacts with a larger system." Alan Freedman, "The Computer Glossary" 268 (8th ed. 1998). A module comprises a machine or machines executable instructions. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also include software-defined units or instructions, that when executed by a processing machine or device, transform data stored on a data storage device from a first state to a second state. An identified module of executable code may, for instance, comprise one or more physical or logical blocks of computer instructions which may be organized as an object, procedure, or function. Nevertheless, the executables of an identified module need not be physically located together, but may comprise disparate instructions stored in different locations which, when joined logically together, comprise the module, and when executed by the processor, achieve the stated data transformation.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single dataset, or may be distributed over different locations including over different storage devices.

Figure 1:
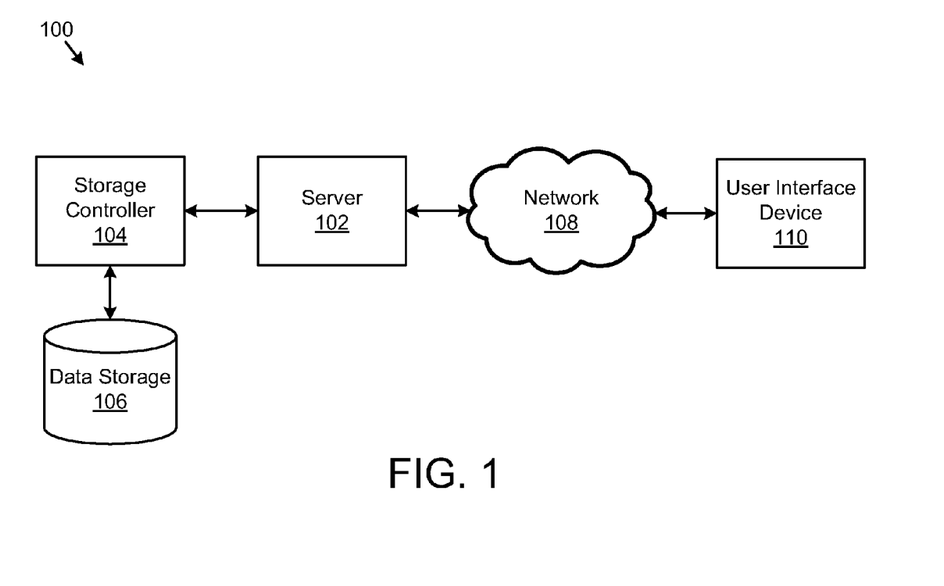
FIG. 1 is a schematic block diagram illustrating one embodiment of a system for data processing.

FIG. 1 illustrates one embodiment of a system 100 for parallel processing of data. The system 100 may include a server 102, a data storage device 104, a network 108, and a user interface device 110. In a further embodiment, the system 100 may include a storage controller 106, or storage server configured to manage data communications between the data storage device 104, and the server 102 or other components in communication with the network 108. In an alternative embodiment, the storage controller 106 may be coupled to the network 108.

In one embodiment, the user interface device 110 is referred to broadly and is intended to encompass a suitable processor-based device such as a desktop computer, a laptop computer, a Personal Digital Assistant (PDA), a tablet computer, a mobile communication device or organizer device having access to the network 108. In a further embodiment, the user interface device 110 may access the Internet to access a web application or web service hosted by the server 102 and provide a user interface for enabling a user to enter or receive information.

The network 108 may facilitate communications of data between the server 102 and the user interface device 110. The network 108 may include any type of communications network including, but not limited to, a direct PC to PC connection, a local area network (LAN), a wide area network (WAN), a modem to modem connection, the Internet, a combination of the above, or any other communications network now known or later developed within the networking arts which permits two or more computers to communicate, one with another.

In one embodiment, the server 102 is configured to receive a dataset; determine a control number of a processing system, where the control number comprises a number of evaluation units within the processing system; process the dataset using a plurality of evaluation units; where processing the dataset includes: allocating a free evaluation unit to form a busy evaluation unit; creating a data subdivision for the busy evaluation unit, the data subdivision comprising a part of the dataset; evaluating the data subdivision; and releasing the busy evaluation unit; where allocating, creating, evaluating, and releasing are performed concurrently by the plurality of evaluation units.

Additionally, the server may access data stored in the data storage device 104 via a Storage Area Network (SAN) connection, a LAN, a data bus, or the like. As discussed in further detail below, received data may be received by such networks and busses and stored in data storage device 104.

The data storage device 104 may include a hard disk, including hard disks arranged in an Redundant Array of Independent Disks (RAID) array, a tape storage drive comprising a magnetic tape data storage device, an optical storage device, or the like. In one embodiment, the data storage device 104 may store healthcare related data, such as insurance claims data, consumer data, or the like. However, data storage 104 is not limited to simply storing healthcare related and may store, for example any dataset for data processing. The data may be arranged in a database and accessible through Structured Query Language (SQL) queries, or other database query languages or operations.

Figure 2:
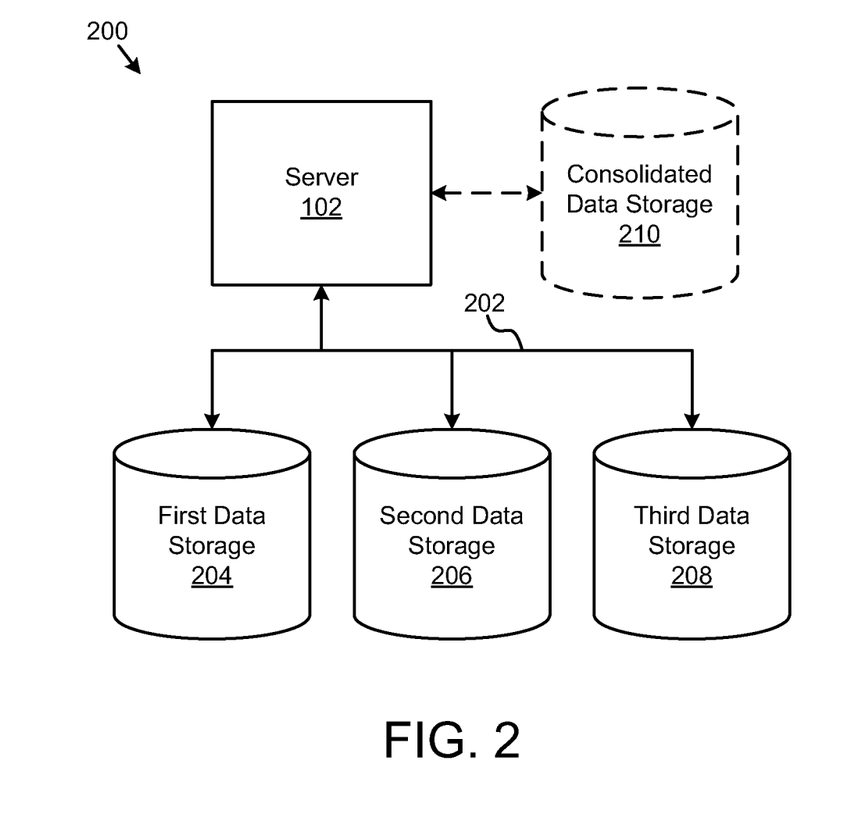
FIG. 2 is a schematic block diagram illustrating one embodiment of a database system for data processing.

FIG. 2 illustrates one embodiment of a data processing system 200 configured to store and manage data for processing data. In one embodiment, the system 200 may include a server 102. The server 102 may be coupled to a data-bus 202. In one embodiment, the system 200 may also include a first data storage device 204, a second data storage device 206 and/or a third data storage device 208. In further embodiments, the system 200 may include additional data storage devices (not shown). In such an embodiment, each data storage device 204-208 may host a separate database of data to be processed. For example, if such information is healthcare claims data, the customer information in each database may be keyed to a common field or identifier, such as an individual's name, social security number, customer number, or the like. Alternatively, the storage devices 204-208 may be arranged in a RAID configuration for storing redundant copies of the database or databases through either synchronous or asynchronous redundancy updates.

In one embodiment, the second data storage device 206 may store summary data associated with the individual. The summary data may include one or more diagnoses of conditions from which the individual suffers and/or actuarial data associated with an estimated cost in medical services that the individual is likely to incur. The third data storage device 208 may store customer service and program service usage data associated with the individual. For example, the third data storage device 208 may include data associated with the individual's interaction or transactions on a website, calls to a customer service line, or utilization of a preventative medicine health program. A fourth data storage device (not shown) may store marketing data. For example, the marketing data may include information relating to the individual's income, race or ethnicity, credit ratings, etc. In one embodiment, the marketing database may include marketing information available from a commercial direct marketing data provider.

In some embodiments, the data storage devices, in addition to storing data to be processed, may further store necessary instructions for increased configurability of the disclosed systems, methods, and apparatuses. As discussed in more detail below, these instructions may be included user supplied instructions (e.g., in an XML file) to configure certain strategies and algorithms that may be used for data processing. Furthermore, in some embodiments, the data storage device may further store various variables of the data processing systems. For example, the system may comprise a variable number of processors (e.g., computer processors and the like) each with varying capacities and capabilities. As such, the variables associated with the availability of computing resources may be stored in the data storage devices.

In one embodiment, the server 102 may submit a query to selected data storage devices 204-208 to collect a consolidated set of data elements associated with an individual or group of individuals. The server 102 may store the consolidated dataset in a consolidated data storage device 210. In such an embodiment, the server 102 may refer back to the consolidated data storage device 210 to obtain a set of data elements associated with a specified individual. Alternatively, the server 102 may query each of the data storage devices 204-208 independently or in a distributed query to obtain the set of data elements associated with a specified individual. In another alternative embodiment, multiple databases may be stored on a single consolidated data storage device 210.

In various embodiments, the server 102 may communicate with the data storage devices 204-210 over the data-bus 202. The data-bus 202 may comprise a SAN, a LAN, or the like. The communication infrastructure may include Ethernet, Fibre-Chanel Arbitrated Loop (FC-AL), Small Computer System Interface (SCSI), and/or other similar data communication schemes associated with data storage and communication. For example, the server 102 may communicate indirectly with the data storage devices 204-210; the server first communicating with a storage server or storage controller 106.

The server 102 may host a software application configured for processing data. The software application may further include modules for interfacing with the data storage devices 204-210, interfacing a network 108, interfacing with a user, and the like. In a further embodiment, the server 102 may host an engine, application plug-in, or application programming interface (API). In another embodiment, the server 102 may host a web service or web accessible software application.

Figure 3:
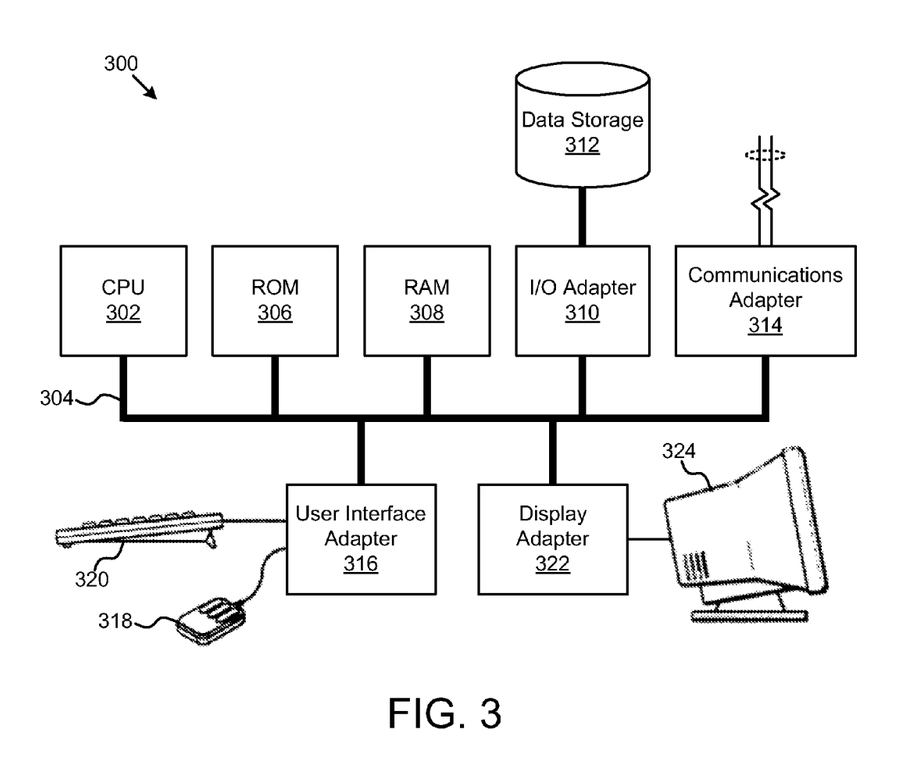
FIG. 3 is a schematic block diagram illustrating one embodiment of a computer system that may be used in accordance with certain embodiments of the system for data processing.

FIG. 3 illustrates a computer system 300 adapted according to certain embodiments of the server 102 and/or the user interface device 110. The central processing unit (CPU) 302 is coupled to the system bus 304. The CPU 302 may be a general purpose CPU or microprocessor. The present embodiments are not restricted by the architecture of the CPU 302, so long as the CPU 302 supports the modules and operations as described herein. The CPU 302 may execute the various logical instructions according to the present embodiments. A single CPU 302 is disclosed in the depicted embodiment, but certain embodiments of the invention have more than one CPU 302 or other processing device.

The computer system 300 also may include Random Access Memory (RAM) 308, which may be SRAM, DRAM, SDRAM, or the like. The computer system 300 may utilize RAM 308 to store the various data structures used by a software application configured to processing data. The computer system 300 may also include Read Only Memory (ROM) 306 which may be PROM, EPROM, EEPROM, optical storage, or the like. The ROM may store configuration information for booting the computer system 300. The RAM 308 and the ROM 306 hold user and system 100 data.

The computer system 300 may also include an input/output (I/O) adapter 310, a communications adapter 314, a user interface adapter 316, and a display adapter 322. The I/O adapter 310 and/or user the interface adapter 316 may, in certain embodiments, enable a user to interact with the computer system 300 in order to input information. In a further embodiment, the display adapter 322 may display a graphical user interface associated with a software or web-based application for processing data.

The I/O adapter 310 may connect to one or more storage devices 312, such as one or more of a hard drive, a Compact Disk (CD) drive, a floppy disk drive, a tape drive, to the computer system 300. The communications adapter 314 may be adapted to couple the computer system 300 to the network 106, which may be one or more of a LAN and/or WAN, and/or the Internet. The user interface adapter 316 couples user input devices, such as a keyboard 320 and a pointing device 318, to the computer system 300. The display adapter 322 may be driven by the CPU 302 to control the display on the display device 324.

The present embodiments are not limited to the architecture of system 300. Rather the computer system 300 is provided as an example of one type of computing device that may be adapted to perform the functions of a server 102 and/or the user interface device 110. For example, any suitable processor-based device may be utilized including without limitation personal data assistants (PDAs), computer game consoles, and multi-processor servers. Moreover, the present embodiments may be implemented on application specific integrated circuits (ASIC) or very large scale integrated (VLSI) circuits. In fact, persons of ordinary skill in the art may utilize any number of suitable structures capable of executing logical operations according to the described embodiments.

Furthermore, as shown, the server 102 is shown as a single server. In some embodiments, the processing devices are highly scalable. For example, suitable processors may not only include a single server but a plurality of processing devices (e.g., multi-processor server, multiple multi-processor servers, and the like). In some embodiments, the processing devices may comprise cloud computing technologies to further scale the availability of computing resources. For example, in some embodiments of the disclosed invention, a processing device may comprise a network of processing devices with variable computing resources.

Figure 4:
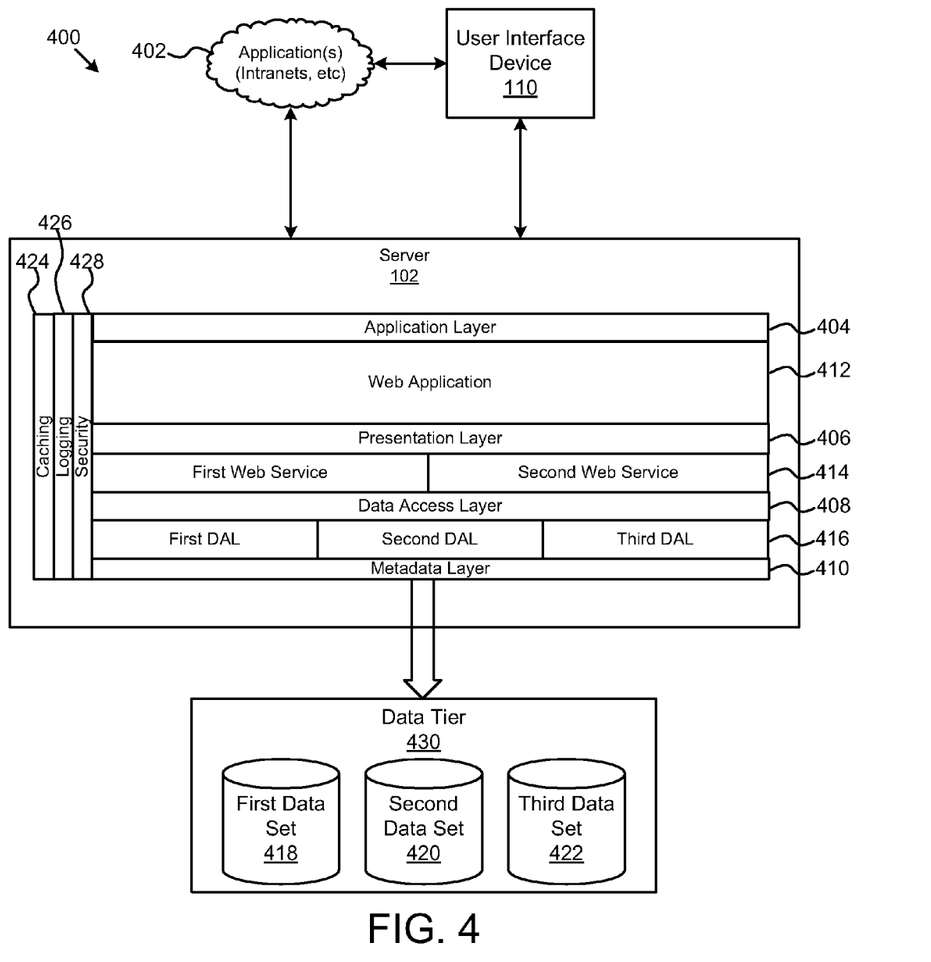
FIG. 4 is a schematic logical diagram illustrating one embodiment of abstraction layers of operation in a system for processing data.

FIG. 4 illustrates one embodiment of a network-based system 400 for processing data. In one embodiment, the network-based system 400 includes a server 102 (e.g., including a plurality of multi-processor servers). Additionally, the network-based system 400 may include a user interface device 110. In still a further embodiment, the network-based system 400 may include one or more network-based applications 402 configured to be operated over a network 108 including an intranet, the Internet, or the like. In still another embodiment, the network-based system 400 may include one or more data storage devices 104.

The network-based system 400 may include components or devices configured to operate in various network layers. For example, the server 102 may include modules configured to work within an application layer 404, a presentation layer 406, a data access layer 408 and a metadata layer 410. In a further embodiment, the server 102 may access one or more datasets 418-422 that comprise a data layer or data tier 430. For example, a first dataset 418, a second dataset 420 and a third dataset 422 may comprise a data tier 430 that is stored on one or more data storage devices 204-208.

One or more applications 412 (e.g., a web application, application accessible across a network, or the like) may operate in the application layer 404. For example, a user may interact with the application 412 though one or more I/O interfaces 318, 320 configured to interface with the application 412 through an I/O adapter 310 that operates on the application layer. In one particular embodiment, an application 412 may be provided for processing data that includes software modules configured to perform the steps of receiving a dataset; determining a control number of a processing system (where the control number comprises a number of evaluation units within the processing system); processing the dataset using a plurality of evaluation units (where processing the dataset includes: allocating a free evaluation unit to form a busy evaluation unit; creating a data subdivision for the busy evaluation unit; evaluating the data subdivision; and releasing the busy evaluation unit). Moreover, the allocating, creating, evaluating, and releasing are performed concurrently by the plurality of evaluation units.

In a further embodiment, the server 102 may include components, devices, hardware modules, or software modules configured to operate in the presentation layer 406 to support one or more web services 414. For example, an application 412 may access or provide access to a web service 414 to perform one or more web-based functions for the application 412. In one embodiment, an application 412 may operate on a first server 102 and access one or more web services 414 hosted on a additional servers (not shown) during operation.

In one embodiment, an application 412 or a web service 414 may access one or more of the datasets 418-422 through the data access layer 408. In certain embodiments, the data access layer 408 may be divided into one or more independent data access layers 416 for accessing individual datasets 418-422 in the data tier 412. These individual data access layers 416 may be referred to as data sockets or adapters. The data access layers 416 may utilize metadata from the metadata layer 410 to provide the application 412 or the web service 414 with specific access to the dataset 412.

For example, the data access layer 416 may include operations for performing a query of the datasets 418-422 to retrieve specific information for the application 412 or the web service 414. In a more specific example, the data access layer 416 may include a query for status update regarding a particular subdivision of data processing.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Furthermore, each of the various method steps disclosed herein may be implemented as a software module. Similarly, one or more steps may be grouped together to form one such software module. A computer program product configured to process data may be comprised of one or more of these software modules. In some embodiments, the server 102 may be configured to execute one or all of the method steps described here.

Figure 5:
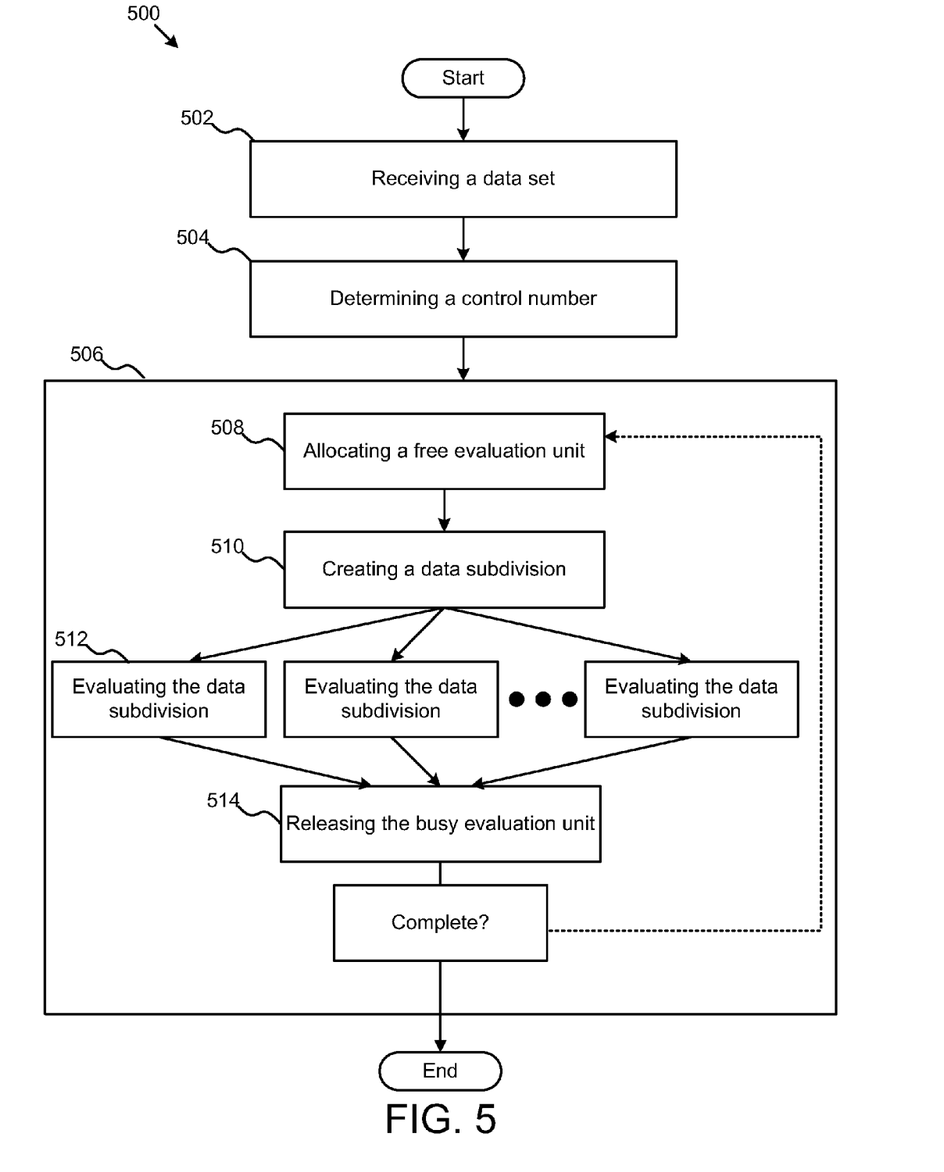
FIG. 5 is a schematic block diagram illustrating one embodiment of a method for processing data.

FIG. 5 illustrates one embodiment of a method 500 for processing data. In one embodiment, the method 500 starts by receiving 502 a dataset. As described in detail with respect to FIG. 2, the dataset may be received across a network and subsequently stored in one or more various storage devices. In some embodiments, receiving a dataset may simply comprise accessing a dataset that may be stored at a specific network location. For example, one or more datasets to be processed may be stored at a remote data storage device. Rather than transferring all of the data across the network, the data may be accessed from the remote storage device and transferred as required.

As used herein, a "dataset" is a collection of data to be processed. A dataset may organized as plurality of tasks to be processed. For example, a healthcare claim may include missing or incorrect information, and a particular task may include compiling and/or correcting that information from the appropriate database to update the information in the healthcare claim. As explained, however, a dataset can include any data to be processed—not simply healthcare data. Other applications—such as a financial institution doing end of day book reconciliations for funds transfers/stock orders—may benefit from the data processing methods, systems, and apparatuses disclosed herein. A particular dataset may also be considered to have one or more dataset elements, wherein each dataset element may characterized by the type of data stored. For example, a dataset of healthcare claims may include dataset elements in such categories as patient identifiers, provider identifiers, claim identifiers, and the like.

Figure 6:
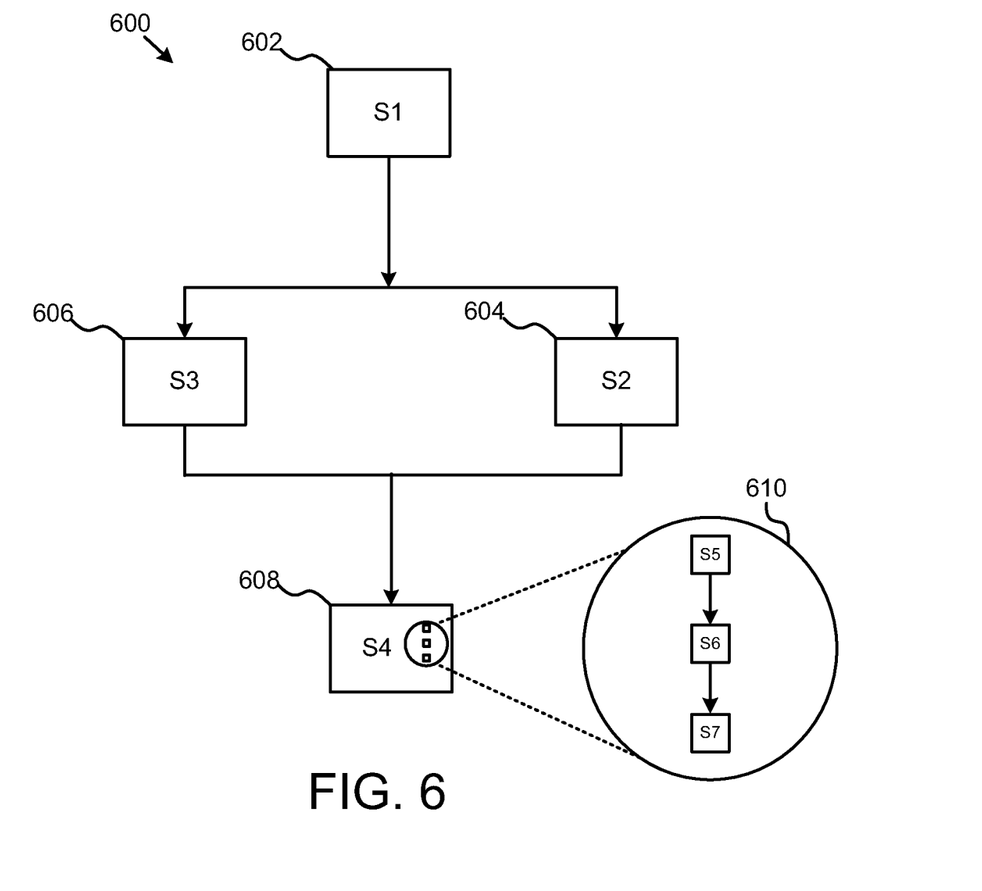
FIG. 6 is a schematic block diagram illustrating a task and subtasks within a dataset.

As shown with respect to FIG. 6, a particular task 600, may include additional subtasks 602-608. In some embodiments, tasks may be defined recursively. That is, each task may include additional subtasks, and each subtask may include additional subtasks. For example, as shown in the figure, subtask 608 further comprises additional subtasks 610. Furthermore, tasks and subtasks may include ordering dependencies. As shown with respect to FIG. 6, subtask S1 must be performed before S2 and S3. Subtask S2 and S3, however, may be completed in any order, and as shown can be completed in parallel. Subtask S4 cannot begin until the completion of subtask both S2 and S3. The evaluation of subtasks with dependencies will be discussed in more detail below. In some embodiments, tasks may be nested within tasks. In some embodiments, the tasks and subtask may be organized using an XML (or other like configuration framework).

A particular dataset to be processed may include thousands, millions, billions, or more tasks. In some embodiments of the method, particular details regarding the number of tasks and subtasks may be unknown. For example, the precise size of the dataset to be processed may be unknown before the processing of the dataset begins. As described in more detail below, such a feature allows the dataset to be incrementally subdivided and processed as required.

The method 500 may proceed by determining 504 a control number of a processing system. As used in herein, an evaluation unit is a discrete computing resource used to process a dataset. As discussed in detail above, a server 102 may comprise one or more processing devices. For example, in various embodiments, an evaluation unit may comprise a single CPU, a single server, a multi-process server, and/or a cloud computing resource. In some embodiments, multiple processing units may be comprised in a single processing device. Thus, evaluation units need not be physically discrete from one another. In some embodiments, the control number may comprise a number of evaluation units within the processing system. In some embodiments, the control number defines the maximum number of evaluation units that may be used to concurrently process data.

In a simple example, a processing system comprising four processing devices may be determined to have a control number of 4. As such, the processing system could be described as having four evaluation units capable of concurrently processing data. In practice, the determination of a control number will often be more complicated. In some embodiments, determining a control number may comprise determining the number of available computing resources. For example, these various computing resources may include the memory size and/or the processing capability (e.g., the number and speed of CPUs) of each of the one or more processing devices that make up the processing system. Moreover, the sum of the computing resources may also be considered when determining control number.

In some embodiments, the control number is determined in response to various configuration rules. Configuration rules may be pre-defined (e.g., through an XML framework or other configuration file) by a user and received by the method 500. In some embodiments, the configuration rules may define the minimum and/or maximum computing resources required for each evaluation unit. In response to the available computing resources and within the bounds of the configuration file, a control number may be determined. In some embodiments, determining the control number may include using one or more configurable control number strategies. A control number strategy may include known programming strategies used to determine the available resources within a computing system and may apply the configuration rules. Notably, the control number strategy is configurable, and various different logical modules and strategies may be used to determine a control number.

A configuration rule that may be used with certain embodiments of the invention may include the use of a specific mathematical formula in response to the number of processing devices (e.g., CPUs) and the amount of memory. A specific example of a control number configuration rule follows for a given system:

$$\text{Control number} = N^*(\text{Number of CPUs}) + M^*(\text{Number of gigabytes of memory})$$

wherein N and M are user selected variables. Applying this formula where N is 4 and M is 1 for a system with 4 CPUs and 20 gigabytes of memory, the control number would be: 4*(4)+1*(20)=36.

The method 500 may proceed by processing 506 the dataset. Generally, processing the dataset may include evaluating each of the tasks in the dataset using a plurality of evaluation units—concurrently. Processing 506 the dataset may first include allocating 508 a free evaluation unit. As described above, the control number may define the number of evaluation units available for processing in the processing system. At any given time, any such evaluation unit may be characterized as "free" or "busy." A busy evaluation unit is currently evaluating a dataset, and a free evaluation unit is available to evaluate a dataset. Allocating 508 an evaluation unit may include checking whether any evaluation units are free. If an evaluation unit is free, that evaluation unit may be allocated to evaluate a dataset.

Processing 506 the dataset may also include creating 510 a data subdivision for the busy evaluation unit. A data subdivision may comprise a part of the dataset. As described earlier, a data subdivision comprises a plurality of tasks to be processed. A data subdivision may include a grouping of those tasks. In a simple example, a dataset may include 1,000,000 discrete tasks that need to be evaluated, and a particular data subdivision may have 100 of these tasks. Thus, in this example, if each data subdivision has 100 tasks, there would be 10,000 data subdivisions. In some embodiments, the data subdivisions may be incrementally subdivided. Thus, rather than subdividing all 1,000,000 tasks into 10,000 subdivisions before evaluating the tasks, each data subdivision may be created dynamically as resources allow (e.g., as an evaluation unit is free or is expected to be free).

In some embodiments, configurable strategies may be used for subdividing datasets to form data subdivisions. These strategies may be configured and implemented both before and during the processing of a given dataset. As such, based on the number of CPUs, operating system, memory size, and/or evaluation times, the configured subdivision strategy may change dynamically. For example, a "null subdivision" strategy may be used, wherein no further subdivision of data is performed. This may be useful where the data is organized recursively (e.g., multiple subtasks nested with subtasks/tasks). An "identification based" strategy may be used based on a unique identification number based on the dataset elements within a dataset. As explained earlier, the various data stored in a dataset may be organized through one or more dataset elements. In some embodiments, each dataset element may have a unique numerical identity. The identification based strategy may be configured to grab N dataset elements at a time (where N represents the control number). As the data subdivisions are created, the range of the new subdivision may begin where the previous subdivision ended. For example if N=100, the first data subdivision would have a range of 1-100, the second 101-200, and so on. The strategy uses the unique numerical identity to find the dataset elements associated with the assigned range. The unique numerical identities need not be contiguous, and thus, the strategy may find all of the dataset elements within the assigned range. The strategy is configurable, and as such, any user defined strategy based on the dataset contents and system specification may be used. User defined subdivision strategies may be based on anything within the dataset, computing environment (CPUs, memory, operating system, or the like), or prior knowledge. For example, an application may choose to process elements of the dataset in subdivisions based on gender, the number of days the bill is overdue, orders meeting a certain criteria such as by stock symbol, or a combination of criteria (gender, diagnosis, and age).

Processing 506 the datasets may also include evaluating 512 the data subdivision. In some embodiments, evaluating 512 the data subdivision is performed concurrently by the plurality of evaluation units that make up the processing systems. For example, if the control number 4, in some embodiments, four evaluation units will each concurrently evaluate 512 a data subdivision. In some embodiments, once the evaluation 512 of a data subdivision has been completed, the evaluation unit may be released 514. Thus, the released evaluation unit may now be characterized as free. This newly free evaluation unit may be allocated 508, and new data subdivision may be created 510, and the new data subdivision may be evaluated 512. This pattern of allocating, creating, evaluating, and releasing may repeat and run concurrently until the dataset is completely processed.

In some embodiments of the method, status messages may be created and/or sent to inform the status of the data processing. For example, in some embodiments, the evaluation duration time may be estimated and reported. The actual evaluation time may be compared to the evaluation duration time.

In some embodiments, a data subdivision may be characterized as more than simply a collection of tasks. As discussed above, a task and its associated subtasks may include one or more dependencies. As such, in some embodiments, each data subdivision may be characterized as independent of the other data subdivisions. That is, all of the tasks and subtasks within a given data subdivision can be evaluated independent of the other data subdivisions. Thus, a data subdivision may comprise within it the logic to address the various dependencies within the various tasks. Within a data subdivision the completion of a task or a subtask may produce an intermediate result, and that intermediate result may be shared with other dependant subtasks within the data subdivision. Without such data subdivision independence, intermediate results between data subdivision may be persisted to disk storage while another data subdivision is being evaluated. This feature of this embodiment eliminates the performance overhead of persisting intermediate results between dependent steps.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention as defined by the appended claims.

What is claimed is:

1. A method for data processing, the method comprising:
receiving a dataset;
determining a control number of a processing system, where the control number defines a maximum number of evaluation units that can be used to concurrently process the dataset, with each evaluation unit representing a discrete computing resource used to process data;
processing the dataset using a plurality of evaluation units, where processing the dataset comprises:
allocating a free evaluation unit to form a busy evaluation unit;
creating a data subdivision for the busy evaluation unit using one or more configurable subdivision strategies implemented before and during the processing of the dataset;
dynamically modifying, during the processing of the dataset, the one or more configurable subdivision strategies based, at least in part, on contents of the dataset;
evaluating the data subdivision;
creating a status message reporting an estimated duration time for processing the dataset; and
releasing the busy evaluation unit;
wherein the evaluating step is performed concurrently by the plurality of evaluation units.

2. The method of claim 1, where processing the dataset is repeated by the plurality of evaluation units until completion.

3. The method of claim 1, where an evaluation unit comprises one or more processing devices.

4. The method of claim 1, where the data subdivision comprises one or more subtasks.

5. The method of claim 4, where evaluating the data subdivision comprises evaluating one or more subtasks.

6. The method of claim 4, where evaluating the data subdivision further comprises describing the data subdivision with an XML framework.

7. The method of claim 6, where describing the dataset with an XML framework further comprises ordering dependencies of the one or more subtasks to form one or more dependent subtasks.

8. The method of claim 7, where evaluating the data subdivision further comprises:
producing intermediate results; and
sharing the intermediate results with the one or more dependent subtasks.

9. The method of claim 1, where creating the data subdivision comprises recursively creating nested data subdivisions.

10. The method of claim 1, where determining the control number comprises using configuration rules.

11. The method of claim 1, where determining the control number further comprises determining available compute resources.

12. The method of claim 10, where determining the control number further comprises determining available compute resources in response to the configuration rules.

13. The method of claim 11, where determining the control number further comprises determining the control number in response to the memory size and the one or more processing devices.

14. The method of claim 11, further comprising using one or more configurable control number strategies.

15. The method of claim 1, where evaluating the data subdivision further comprises:
estimating the evaluation duration; and
measuring the evaluation duration.

16. The method of claim 15, further comprising sending status messages.

17. A apparatus for data processing, the apparatus comprising: a processor configured to:
receive a dataset;
determine a control number of a processing system, where the control number defines a maximum number of evaluation units that can be used to concurrently process data, with each evaluation unit representing a discrete computing resource used to process data; and
process the dataset using a plurality of evaluation units, where processing the dataset comprises:
allocating a free evaluation unit to form a busy evaluation unit;
creating a data subdivision for the busy evaluation unit using one or more configurable subdivision strategies implemented before and during the processing of the dataset;
dynamically modifying, during the processing of the dataset, the one or more configurable subdivision strategies based, at least in part, on contents of the dataset;
evaluating the data subdivision;
creating a status message reporting an estimated duration time for processing the dataset; and
releasing the busy evaluation unit;
wherein the evaluation step is performed concurrently by the plurality of evaluation units.

18. The apparatus of claim 17, where processing the dataset is repeated by the plurality of evaluation units until completion.

19. The apparatus of claim 17, where an evaluation unit comprises one or more processing devices.

20. The apparatus of claim 17, where the data subdivision comprises one or more subtasks.

21. The apparatus of claim 20, where evaluating the data subdivision comprises evaluating one or more subtasks.

22. The apparatus of claim 20, where evaluating the data subdivision further comprises describing the data subdivision with an XML framework.

23. The apparatus of claim 22, where describing the dataset with an XML framework further comprises ordering dependencies of the one or more subtasks to form one or more dependent subtasks.

24. The apparatus of claim 23, where evaluating the data subdivision further comprises:
producing intermediate results; and
sharing the intermediate results with the one or more dependent subtasks.

25. The apparatus of claim 17, where creating the data subdivision comprises recursively creating nested subdivisions.

26. The apparatus of claim 17, where determining the control number comprises using configuration rules.

27. The apparatus of claim 17, where determining the control number further comprises determining available compute resources.

28. The apparatus of claim 27, where determining the control number further comprises determining available compute resources in response to the configuration rules.

29. The apparatus of claim 28 where determining the control number further comprises determining the control number in response to the memory size and the one or more processing devices.

30. The apparatus of claim 28, where determining the control number further comprising using one or more configurable control number strategies.

31. The apparatus of claim 17, where evaluative the data subdivision further comprises:
estimating the evaluation duration; and
measuring the evaluation duration.

32. The apparatus of claim 31, further comprising sending status messages.

33. A computer program product comprising a non-transitory computer readable medium having computer usable program code executable to perform operations for processing data, the operations of the computer program product comprising:
receiving a dataset;
determining a control number of a processing system, where the control number defines a maximum number of evaluation units that can be used to concurrently process data, with each evaluation unit representing a discrete computing resource used to process data;
processing the dataset using a plurality of evaluation units, where processing the dataset comprises:
allocating a free evaluation unit to form a busy evaluation unit;
creating a data subdivision for the busy evaluation unit using one or more configurable subdivision strategies implemented before and during the processing of the dataset;
dynamically modifying, during the processing of the dataset, the one or more configurable subdivision strategies based, at least in part, on contents of the dataset;
evaluating the data subdivision;
creating a status message reporting an estimated duration time for processing the dataset; and
releasing the busy evaluation unit;

wherein the evaluating step is performed concurrently by the plurality of evaluation units.

\* \* \* \* \*